(12) United States Patent
Kim et al.

(10) Patent No.: US 8,630,696 B2
(45) Date of Patent: Jan. 14, 2014

(54) INTEGRATED PET/CT SYSTEM

(75) Inventors: Yong-Kown Kim, Nonsan (KR); Yong Choi, Seoul (KR); Ki-Sung Lee, Yongin (KR); Hyoung-Uk Choi, Seongnam (KR); Sey-Joon Park, Suwon (KR)

(73) Assignee: Nucare Medical Systems, Inc., Seoul (KR)

( * ) Notice: Subject to any disclaimer, the term of this patent is extended or adjusted under 35 U.S.C. 154(b) by 296 days.

(21) Appl. No.: 12/996,387

(22) PCT Filed: Feb. 25, 2009

(86) PCT No.: PCT/KR2009/000889
§ 371 (c)(1),
(2), (4) Date: Dec. 5, 2010

(87) PCT Pub. No.: WO2009/154340
PCT Pub. Date: Dec. 23, 2009

(65) Prior Publication Data
US 2011/0077511 A1    Mar. 31, 2011

(30) Foreign Application Priority Data
Jun. 17, 2008   (KR) .................. 10-2008-0056923

(51) Int. Cl.
*A61B 6/00* (2006.01)
(52) U.S. Cl.
USPC ............ 600/427; 600/425; 600/436; 378/63; 250/363.03
(58) Field of Classification Search
USPC .................. 600/411, 425, 427, 436; 378/63; 250/363.02, 363.03
See application file for complete search history.

(56) References Cited

U.S. PATENT DOCUMENTS

| | | | |
|---|---|---|---|
| 6,373,916 B1 | 4/2002 | Inoue et al. | |
| 6,449,331 B1 | 9/2002 | Nutt et al. | |
| 6,631,284 B2 | 10/2003 | Nutt et al. | |
| 8,139,713 B2 * | 3/2012 | Janbakhsh | 378/63 |
| 2002/0143249 A1 | 10/2002 | Tornai et al. | |
| 2004/0066909 A1 | 4/2004 | Lonn et al. | |

FOREIGN PATENT DOCUMENTS

KR    10-2007-0090974 A    9/2007

OTHER PUBLICATIONS

Townsend, "A Combined PET/CT Scanner: The Choices," J. of Nuc. Med., vol. 3, pp. 533-534 (2001).
Saoudi et al., "A Novel APD-Based Detector Module for Multi-Modality PET/SPECT/CT Scanners," IEEE Trans in Nuc. Sci., vol. 46, No. 3, pp. 479-484 (1999).
Meikle et al., "Simultaneous Emission and Transmission Measurements for Attenuation Correction in Whole-Body PET," J. of Nuc. Med., vol. 36, No. 9, pp. 1680+ (1995).

* cited by examiner

*Primary Examiner* — Ruth S Smith
(74) *Attorney, Agent, or Firm* — Baker & Hostetler LLP

(57) ABSTRACT

An integrated Positron Emission Tomography (PET)/Computed Tomography (CT) system includes a patient support device supporting a patient pallet, a gantry having a space through which the patient pallet passes, a plurality of integrated PET/CT detector modules attached to one side of the gantry, an x-ray tube attached to the other side of the gantry, and a signal detecting/processing unit. Each of the plurality of integrated PET/CT detector modules include a plurality of PET detectors, a flat-panel x-ray detector disposed in contact with the PET detectors and a read-out driver mounted at a rear end of the PET detectors and electrically connected with the flat-panel x-ray detector.

5 Claims, 3 Drawing Sheets

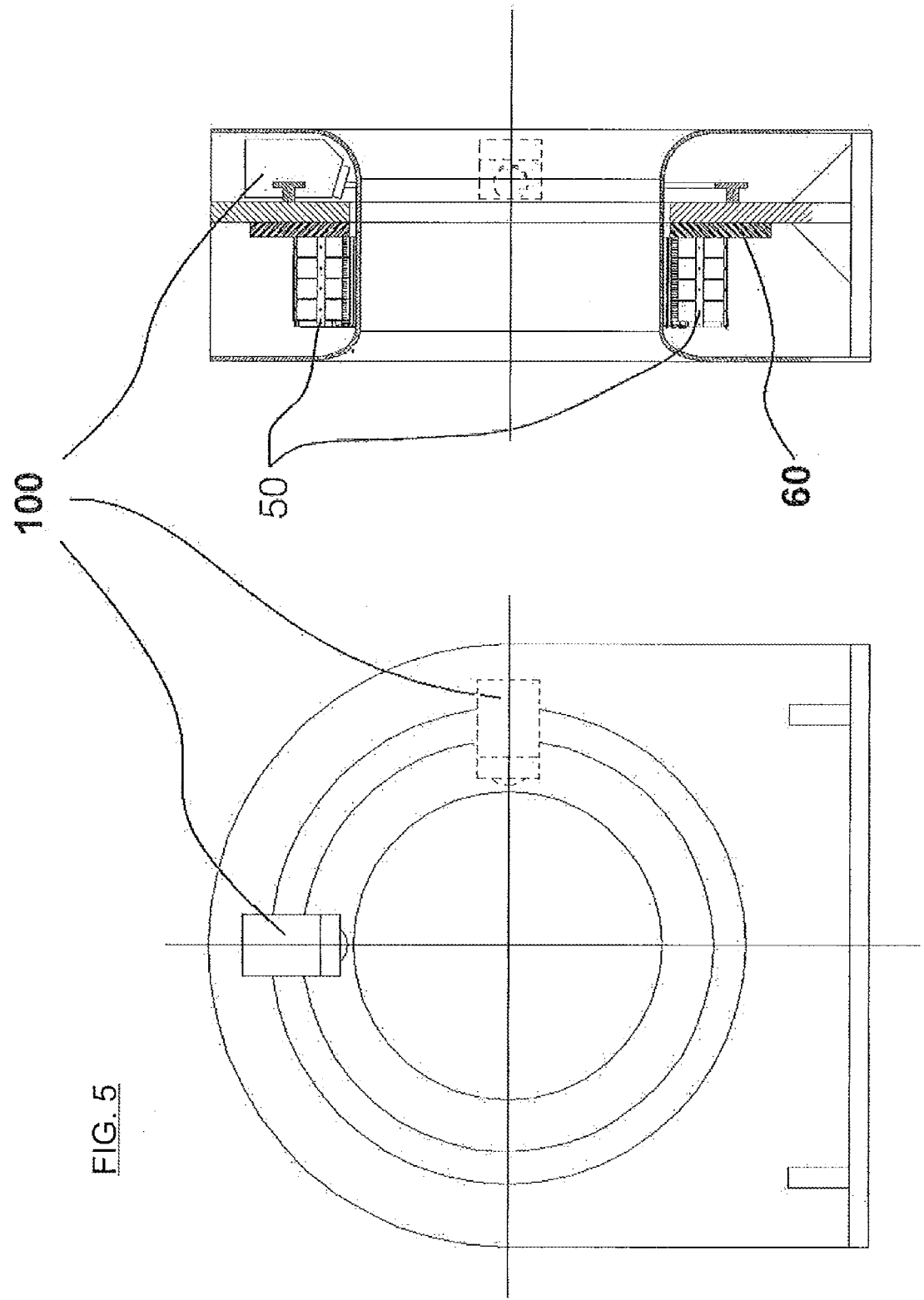

INTEGRATED PET/CT SYSTEM

RELATED APPLICATIONS

This application is a National Stage of International Patent Application PCT/KR2009/000889, filed on Feb. 25, 2009, which claims priority to Korean Patent Application No. 2008 0056923, filed on Jun. 17, 2008 in the Korean Intellectual Property Office, the entire disclosures of which are incorporated herein by reference in their entirety.

BACKGROUND OF THE INVENTION

1. Field of the Invention

The present invention relates to an integrated PET/CT system providing an integrated PET/CT picture by simultaneously sequentially taking a PET picture and a CT picture with one system, and more particularly, to an integrated PET/CT system providing a simple and excellent integrated PET/CT picture by using an integrated PET/CT detecting module formed by integrating a flat-panel x-ray detector with a PET detector.

2. Description of Related Art

Integrated PET/CT composite image apparatuses are medical equipment used for oncology, neurology, cardiovascular medicine and other diagnosis picture and considerably increases diagnosis accuracy by effectively integrating the functional picture provided by the PET and the anatomical picture provided by the CT; therefore, the excellence and necessity has already been clinically proved and demand has rapidly increased in the past several years.

The initial PET and CT composite picture was acquired by simply combining pictures taken by PET and CT systems, but it was difficult to combine the pictures and there were errors in the composite picture because the conditions are different in taking the pictures and movement of patients and organs. Further, patients have to move to two systems at different position to take the pictures, such that there were various problems.

In order to solve the problem, several studies and patents have been proposed around 2000 and representative studies are D W Townsend, "A combined PET/CT scanner: the choices", Journal of Nuclear Medicine, 2001: 3:533-534, and R, Nutt, D W Townsend, "Combined PET and X-ray CT tomograph", U.S. Pat. No. 6,631,284, 2003, which have proposed an integrated PET/CT system by combining PET and CT equipment.

Recently, a demand for the combination product of PET/CT system has been gradually increasing, and the integrated PET/CT products manufactured by combining PET and CT is 95% or more in the entire PET market.

However, the studies and patents of D W Townsend or R. Nutt have proposed simple combination of individual PET system and CT system, which is a little different from an integrated PET/CT system in the true sense of the word.

As shown in FIG. 1, an integrated PET/CT system 91 according to the related art is a product formed by simply combining two apparatuses of a PET apparatus 81 and a CT apparatus 80, which is a little different from the integrated PEC/CT system in the true sense of the word.

Further, since two large apparatuses are combined, the volume of the equipment increases and occupies a large space. Further, the length of the tunnel through which a patient passes to take pictures becomes long, such that the patient's anxiety increases. Further, since a patient has to pass through a long tunnel in the systems of the related art, a relatively long patient pallet 72 was required and accordingly the patient pallet bends when moving to the rear portion of the system, thereby make errors in the pictures.

In order to overcome the problems, the present invention, as shown in FIG. 2, proposes an integrated PET/CT system in the true sense of the word which has a PET and a CT combined in one gantry by using an integrated PET/CT detecting module. The integrated PET/CT equipment takes pictures of the same object in terms of space and time, such that it provides better composite pictures and other advantages by implementing a simple system.

A prior study having a similar concept to the integrated PET/CT proposed in this study has been proposed in U.S. Pat. No. 6,449,331, 2002, titled "Combined PET and CT detector and method for using same", by R. Nutt. However, the basis configuration of the detector and the method of processing pictures are remarkably different from the present invention. The principle of the method proposed in the above patent is to share a common PET detector to take PET and CT pictures and the PET and CT signals are collected and processed through different process circuits. Similarly, there were "A novel APD-Based Detector Module for Multi-Modality PET/SPECT/CT Scanners", by A. Saoudi et. al, IEEE transaction in Nuclear Science, 46:3:479-484, 1999, and "Simultaneous Emission and Transmission Measurements for Attenuation Correction in Whole-Body PET", by SR Meikle, et. al, The Journal of Nuclear Medicine, 36:9:1680-1995. However, in these prior studies, in the same as the proposal of R. Nutt, x-ray pictures are acquired from a common PET detector or a CT picture is acquired by using a gamma ray using a transmission radiation source.

The most important problem of the prior studies and patents is not providing high-resolution CT pictures satisfying the required conditions of recent composite pictures, because the resolutions of the CT picture and the PET detector are the same, and it is difficult to technically implement the composite picture.

A feature of the present invention that is remarkably different from the prior studies and patents is to mount a flat-panel x-ray detector at the front end of a PET detector to acquire CT pictures. As shown in FIG. 3, using the thin flat-panel x-ray detector provides high-resolution CT pictures while minimizing attenuation and scatter of the gamma ray in taking a PET picture.

In general, the flat-panel x-ray detector is mainly used in applications, such as the x-ray angiography or an x-ray digital moving imaging, and recently, a technology implementing an x-ray CT by using the above has been given a patent in the United States, in 2002, by Y. Ionue, et. al. ("X-ray CT apparatus" U.S. Pat. No. 6,373,916). A feature of the CT using the flat-panel x-ray detector is to take a picture of a wide field of view (FOV) without moving a patient by using a wide flat-panel x-ray detector and extending the existing fan beam to an x-ray cone beam.

Describing a difference of the present invention and the patent of Y. Ionue, first, the flat-panel x-ray detector rotates with an x-ray source or tube in the proposal of Y. Ionue. However, in the present invention, as shown in FIG. 5, a PET/CT detector module is mounted and fixed to a stationary gantry and one or a plurality of x-ray tubes rotates along the side of the gantry, which is the fourth generation CT system structure. Further, the size and shape of the flat-panel x-ray detector take the size and shape of the PET, which is also different from the patent of Y. Ionue.

SUMMARY OF THE INVENTION

In order to solve the problem, it is an object of the present invention to implement an integrated PET/CT system in the true sense of word that provides high-resolution CT picture and PET picture having a wide useful field of view (UFOV) by mounting a flat-panel x-ray detector having the same or, if needed, changed shape or increased/decreased size at the front end of a PET detector module composed of a plurality of PET detectors.

It is another object of the present invention to improve the quality of the pictures by minimizing errors that may occur due to movement of the PET and CT detectors, by rotating only one or a plurality of x-ray tube along the side of a gantry while fixing integrated PET/CT detector modules to the gantry.

It is yet another object of the present invention to reduce the system manufacturing cost and the limit in space for installation by implementing a slim system, using one integrated gantry instead of two gantries for CT and PET pictures in the integrated PET/CT equipment, and integrating the other driving components and peripheral devices.

It is still another object of the present invention to minimize fear that a patient passing through a long tunnel feels when performing applications, such as taking a picture of whole body, due to the slim system achieved by reducing the gantry.

It is yet still another object of the present invention to improve quality of pictures by minimizing errors in the pictures due to bending of the patient pallet that is relatively long and longitudinally moves, because a patient has to pass through a long tunnel in the systems of the related art.

It is yet still another object of the present invention to accomplish a new application, such as dynamic imaging in the true sense of word by taking a portion in the same time and space, and provide data correcting errors in the pictures due to organs that during taking pictures, such as the heart and lung.

In order to achieve the objects of the present invention, there is provided an integrated PET/CT system which includes: a patient support device supporting a patient pallet where a patient lies, and being movable longitudinally and up/down; a gantry having a space through which the patient pallet passes, and equipped with an x-ray tube and other driving components; one or more integrated PET/CT detector modules attached to one side of the gantry; one or more x-ray tubes attached to the other side of the gantry and producing x-rays while rotating; a signal detecting/processing unit which processes a PET picture signal and CT picture signal transmitted from the integrated PET/CT detector modules; and a display unit displaying the PET picture signal and the CT picture signal from the signal detecting/processing unit, wherein the gantry and the patient pallet are relatively movable, and the integrated PET/CT detector modules include: a plurality of PET detectors; a flat-panel x-ray detector disposed in contact with the outermost side of the PET detectors in a line with the PET detectors and detecting a picture of the same position; and a read-out driver mounted at the rear end of the PET detector and electrically connected with the flat-panel x-ray detector.

Preferably, the x-ray tube produces fan beams and cone beams and rotates along the gantry.

Preferably, the PET detector includes: a scintillator disposed in contact with the flat-panel x-ray detector; a light guide guiding light in contact with the scintillator; a control circuit disposed in contact with the read-out driver and having a pre-amplifier and a positioning circuit; and PMTs electrically connected in contact with the control circuit, covered by a magnetic shield preventing interference of a magnetic field, and stacked in a plurality of layers.

Preferably, the PET detector includes: a scintillator disposed in contact with the flat-panel x-ray detector; and a solid-state sensor disposed in contact with the scintillator.

Preferably, the shape and area of the flat-panel x-ray detector are the same as the shape and area of the integrated PET/CT detector module.

An integrated PET/CT system proposed by the present invention can individually take a PET or CT picture and can acquire PET and CT pictures sequentially or simultaneously. Further, it can be used for taking picture of animals, pre-clinically as well as clinically.

The PET detector basically uses a PMT that is commonly used, but may use a solid-state detector, if needed.

In general, the PET detector is composed of a scintillator converting a gamma ray into photons, a photomultiplier (PMT) or a solid-state photo sensor which converts the photons into an electric signal, and a circuit that amplifies and processes the electric signal of the photomultiplier and the solid-state photo sensor.

The scintillator used in the PET may be LSO, LYSO, BGO, MLS etc., and according to the method of determining reaction position of gamma rays in the PET detector, the scintillator may be used in a pixel type, a single slab of scintillator type, and a type of divided layers for decoding of DOI (depth of interaction).

The photomultiplier (PMT) or the solid-state photo sensor may be used to convert the photons produced by the scintillator into an electric signal and check the reaction position of the gamma ray in the scintillator. FIG. 3 shows when a PET module is formed by integrating a plurality of PET detectors, particularly using a photomultiplier and a flat-panel x-ray detector mounted at the front end.

One module is achieved by the plurality of PET detectors and an axial FOV of about 15~20 cm is ensured by usually integrating three or four individual detectors.

As described above, the flat-panel x-ray detector is mounted at the front end of the PET module, in which an amplifying circuit or a read-out (R/O) circuit are positioned at the rear end of the detector, except for the x-ray detector (i.e. the portion applied with TFT (thin film transistor) and the scintillator), in order to minimize attenuation and scatter of the gamma ray. The shape and size of the flat-panel x-ray detector is made the same as those of the PET detector to implement the same FOV. However, if needed, the shape and size of the flat-panel x-ray detector may be different from those of the PET, in accordance with the specifications of the CT system design.

Accordingly, the problem that may occur by positioning the x-ray detector at the front end of the PET detector may be attenuation and scatter of the gamma ray due to the x-ray detector in acquiring a PET picture.

As a result of Monte-carlo simulation, as shown in Table 1, assuming that the flat-panel x-ray detector is made of a TFT panel (thin film transistor panel) and scintillation material is applied and a photo-peak window of 25% is generally used in taking a PET picture of 511 keV, it is expected that the gamma ray scatter ratio increases by about 1.3%.

Further, according to examination of an attenuation ratio, it is examined that the gamma ray of 511 keV is attenuated by around 7% by the x-ray panel, such that it is expected that combination of the flat-panel x-ray substantially does not deteriorate the quality of the PET picture and sensitivity.

The integrated PET/CT detector module is mounted in a circular gantry, as shown in FIG. 4, to form a stationary PET/CT system, in which the radius between the detectors is about 70~80 cm such that it is possible to take a picture of a normal adult. However, when the equipment is developed for a brain, small animals, and other organs, the radius may be increased or decreased, if necessary.

As for the x-ray tube for taking CT pictures, as shown in FIG. 5, one or a plurality of x-ray tubes are attached and rotated at the sides of the gantry (they are positioned at the rear portion in FIG. 5, but may be positioned at the front portion, if needed). The specifications including the rotational speed and the energy of x-rays, and the shape of beams are designed to be changed in accordance with applications.

The patient pallet of the patient support is preferably made of a material that minimizes attenuation by the x-rays and the gamma rays and should be designed such that only the portion corresponding to the patient pallet of the patient support can pass through the tunnel when a patient passes through the tunnel. This can be implemented by moving longitudinally only the patient pallet while the patient support slides, or moving longitudinally the entire support supporting the patient pallet, or moving longitudinally the entire gantry.

TABLE 1

| Materials | 511 keV | |
| --- | --- | --- |
| | All spectrum | 25% PP window |
| Plastic (2 mm) | 1.9% | 0.30% |
| CsI(T1) (2 mm) | 6.1% | 1.4% |

As described above, the integrated PET/CT system of the present invention provides better composite pictures than the existing PET/CT systems and increases diagnostic accuracy by basically providing functional PET pictures and anatomical CT pictures with an integrated PET/CT detector.

Further, it does not substantially need to longitudinally move a patient sequentially by using the flat-panel x-ray detector having a wide axial FOV in acquiring CT pictures.

Since a picture of the same organ is taken at the same time by the PET/CT system proposed by the present invention, it is possible to simultaneously or sequentially take the PET and CT pictures.

It is possible to develop various new applications, including a new type of dynamic image that functionally and anatomically changes according to time of specific organs Further, it is possible to reduce the manufacturing cost of the system and the spatial limit for installing the system and improve convenience for patients by integrating the peripheral devices and driving components, by implementing an integrated slim PET/CT system.

BRIEF DESCRIPTION OF THE DRAWINGS

The above and other objects, features and other advantages of the present invention will be more clearly understood from the following detailed description taken in conjunction with the accompanying drawings, in which:

FIG. 5 is a view schematically showing when an x-ray source rotates in the integrated PET/CT system shown in FIG. 2.

DETAILED DESCRIPTION OF THE INVENTION

Hereinafter, an integrated PET/CT system according to a preferred embodiment of the present invention is described in detail with reference to the accompanying drawings.

Figure 1:
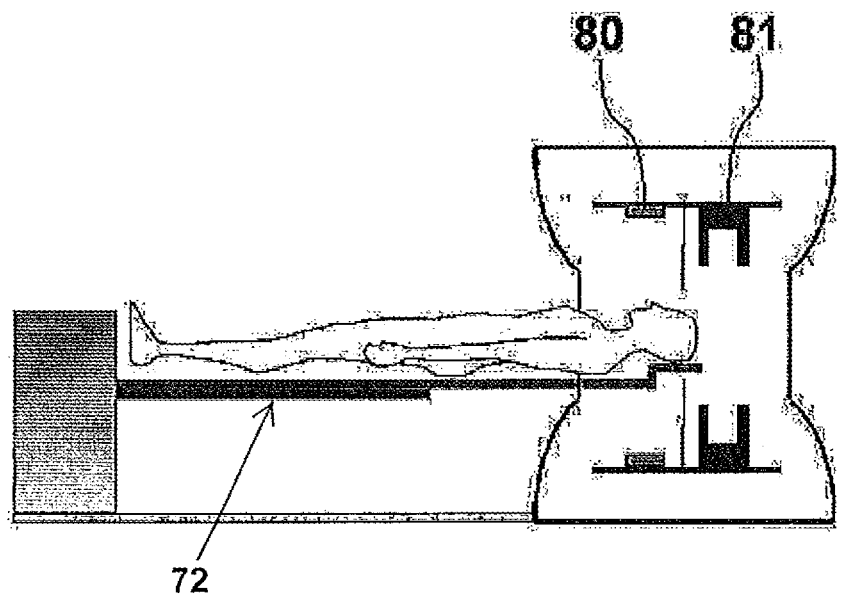
FIG. 1 is a view schematically showing an integrated PET/CT system according to the related art.
Figure 2:
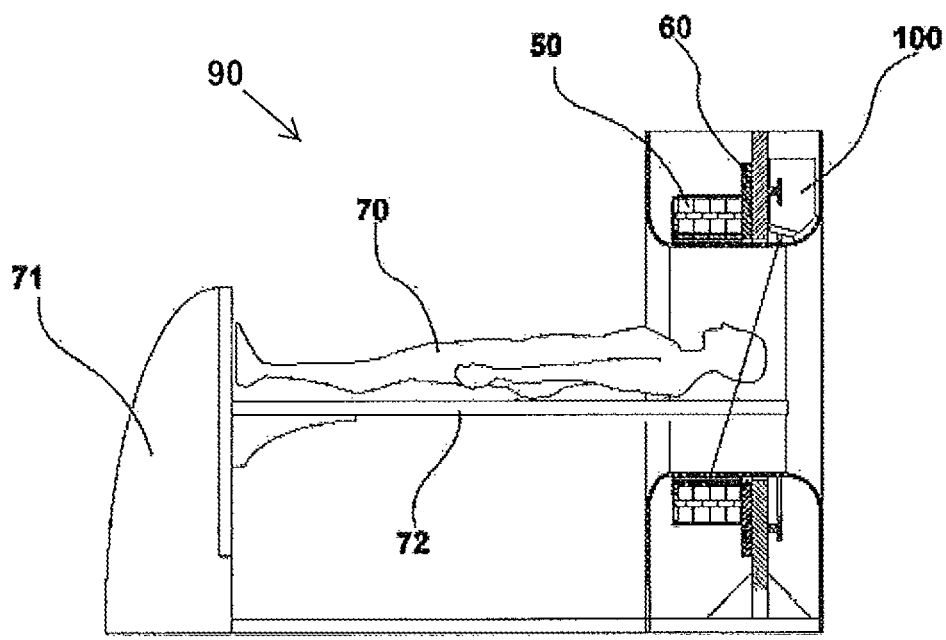
FIG. 2 is a view schematically showing an integrated PET/CT system according to an embodiment of the present invention.
Figure 3:
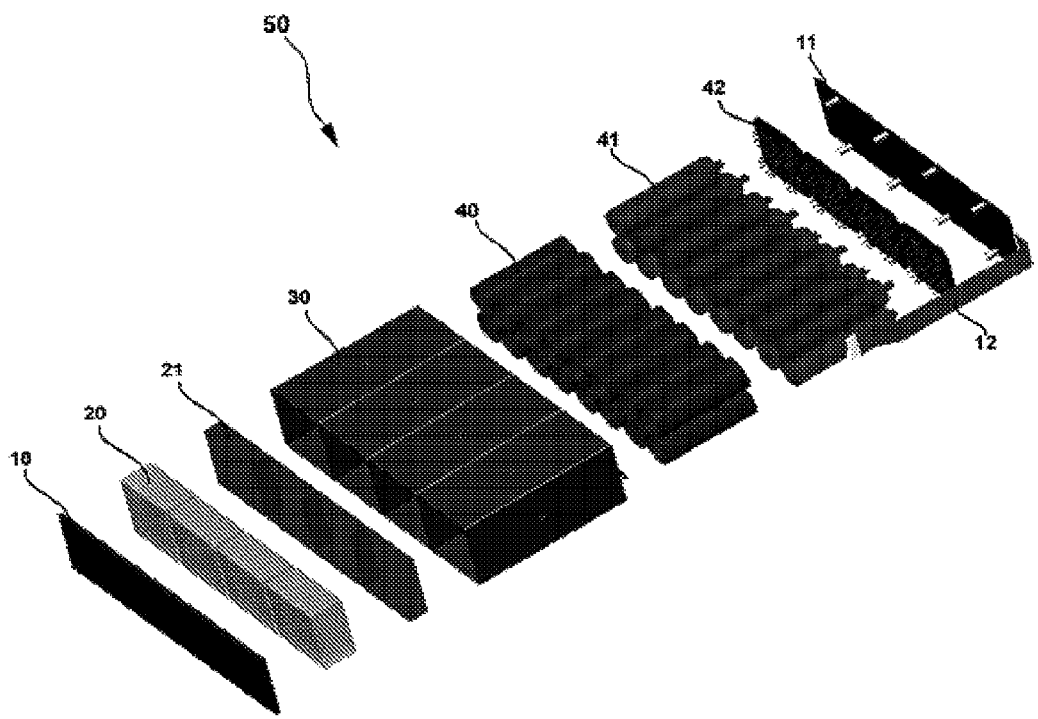
FIG. 3 is an exploded perspective view showing an integrated PET/CT detector used in the integrated PET/CT system shown in FIG. 2.
Figure 4:
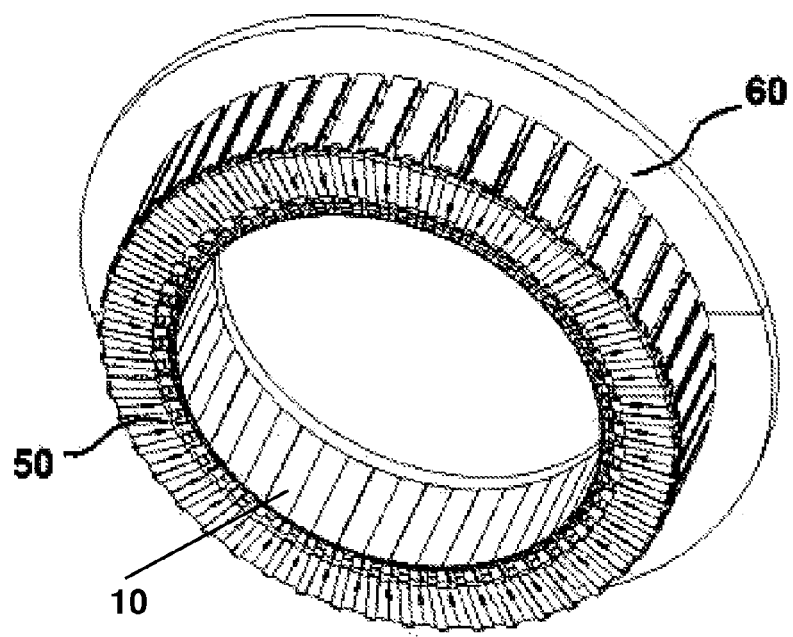
FIG. 4 is a perspective view showing when the integrated PET/CT detector shown in FIG. 3 is combined with a gantry.

FIG. 2 is a view schematically showing an integrated PET/CT system according to an embodiment of the present invention, FIG. 3 is an exploded perspective view showing an integrated PET/CT detector used in the integrated PET/CT system shown in FIG. 2, FIG. 4 is a perspective view showing when the integrated PET/CT detector shown in FIG. 3 is combined with a gantry, and FIG. 5 is a view schematically showing when an x-ray source rotates in the integrated PET/CT system shown in FIG. 2.

The integrated PET/CT system 90 according to an embodiment of the present invention, as shown in FIG. 2, is an integrated PET/CT system in the true sense of word which includes various advantages by being implemented in a slim type, using an integrated PET/CT detector module 50 having a flat-panel x-ray detector.

The integrated PET/CT system can simultaneously acquire CT pictures and PET pictures with a wide axial FOV in the one space, such that it has excellence by being more useful for the existing PET/CT picture application and accomplishing a new application. Further, the concept proposed by the present invention can be used for pre-clinical systems as well as clinical systems.

The integrated PET/CT detector module 50, which is the most important component of the present invention, as shown in FIG. 3, is formed by combining a plurality of PET detectors with a flat-panel x-ray detector 10.

The flat-panel x-ray detector 10 is positioned at the front end of the integrated PET/CT detector module 50 and the read-out driver 11 of the x-ray detector is positioned at the rear end of the integrated PET/CT detector module 50, in order to minimize attenuation and scatter of the gamma rays in taking a PET picture during operation of the flat-panel x-ray detector 10.

The flat-panel x-ray detector 10 and the read-out driver 11 are electrically connected by a cable 12. An FPCB (flexible printed circuit board) may be used, instead of the cable 12.

The size of the flat-panel x-ray detector 10 basically takes the shape and size of the integrated PET/CT detector module 50, but in some cases, it may be reduced smaller than that of the integrated PET/CT detector module 50 or other shapes may be possible.

Further, the flat-panel x-ray detector 10 may be manufactured to extend throughout a plurality of PET modules.

The plurality of PET detectors basically includes a scintilator 20 disposed in contact with the flap-panel x-ray detector 10, a light guide 21 disposed in contact with the scintillator 20, a control circuit 42 disposed in contact with the read-out driver 11 and having a pre-amplifier and a positioning circuit, and PMTs 41 electrically connected in contact with the control circuit 42, covered by a magnetic shield 40 preventing interference of a magnetic field, and stacked in a plurality of layers.

The PMTs 41 covered by the magnetic shield 40 are accommodated, fixed, and packed in an internal space of a housing 30.

Further, when a solid-state photo-sensor (not shown) is used in the PET detector, the PMTs 41, and the light guide 21, housing 30, and magnetic shield 40, which are sub-components for the PMTs, are not necessary, and the scintillator 20 and the solid-state photo sensor (not shown) are directly combined, such that it is possible to achieve a PET detector module having a simple structure and small volume.

The solid-state detector is not influenced by a magnetic field, such that it can be useful when the system expands and is combined with an MRI apparatus etc.

A pixel type scintillation crystal or a single scintillation crystal may be used for the scintillator 20 used in the PET detector, and the size and the gap of the pixels are designed to fit to a desired resolution in the pixel type, and the light guide 21 may not be provided in some cases.

In the embodiment of the present invention, although one module is composed of four PET detectors, in general, it is possible to ensure desired-sized axial FOV by combining predetermined number of PET detectors.

FIG. 4 shows when the integrated PET/CT detector modules 50 assembled as described above are mounted adjacent to each other along the circumference of the gantry 60. In this structure, the flat-panel x-ray detector 10 is arranged toward the center of the gantry 60. The number of the flat-panel x-ray detectors 10 is 50 in FIG. 4.

The radius of the gantry 60 depends on the usage of the system, and about 70 to 80 cm is suitable such that a normal adult can pass in a common clinic PET/CT. If it is manufactured for only brains or pre-clinic, the radius of the gantry, the size and resolution of the PET/CT detector, and the number of the PET/CT detectors combined with the PET/CT modules (i.e. the number of the PET detector rings) can be appropriately adjusted, in accordance with the applications.

Further, basically, the gantry 60 equipped with the integrated PET/CT detector module 50 is a stationary type, which does not rotate.

The integrated PET/CT detector module 50 having the above configuration is attached to one side of the gantry 60 and an x-ray tube 100 is attached to the other side of the gantry 60, such that the integrated PET/CT system according to an embodiment of the present invention is achieved.

Further, the integrated PET/CT system may be equipped with a patient support device 71 having a patient pallet 72 such that a patient 70 can lay down.

In this configuration, the gantry 60 is fixed and the patient pallet 72 is movable, whereas the patient support device 71 and the patient pallet 72 may be movable and the gantry 60 may be conveyed.

Further, though not shown in drawings, the integrated PET/CT system includes a signal detecting/processing unit that processes a PET picture signal and CT picture signal acquired from the integrated PET/CT detector module 50 and a display unit that displays the PET picture signal and the CT picture signal from the signal detecting/processing unit.

The patient pallet 72 is preferably made of a material that minimizes attenuation and scatter and is movable longitudinally and up/down.

As shown in FIG. 5, the x-ray tube 100 is positioned at a side of the gantry 60 and produces fan beams or cone beams while circumferentially rotating. Although the x-ray tube 100 is positioned at the rear portion of the gantry in FIG. 5, it may be positioned at the front portion thereof in another embodiment.

The driving speed, the intensity of the x-rays, and filtering option and other specification of the x-ray tube 100 can be adjusted in accordance with the application.

Further, it does not substantially need to longitudinally move a patient sequentially by combining the flat-panel x-ray detector having a wide axial FOV with a cone beam x-ray, in acquiring CT pictures.

The integrated PET/CT system can simultaneously or sequentially acquire PET and CT pictures of organs as the pictures that are taken, provide better composite pictures, and makes it possible to implement a simple system.

While the present invention has been described with reference to the preferred embodiments, it will be understood by those skilled in the related art that various modifications and variations may be made therein without departing from the scope of the present invention as defined by the appended claims.

What is claimed is:

1. An integrated Positron Emission Tomography (PET)/Computed Tomography (CT) system comprising:
   a patient support device supporting a patient pallet, and being movable longitudinally and up/down;
   a gantry having a space through which the patient pallet passes, and equipped with an x-ray tube and a driving component;
   a plurality of integrated PET/CT detector modules attached to one side of the gantry;
   the x-ray tube attached to the other side of the gantry and producing x-rays while being rotated by the driving component;
   a signal detecting/processing unit which processes a PET picture signal and CT picture signal transmitted from the integrated PET/CT detector modules; and
   a display unit displaying the PET picture signal and the CT picture signal from the signal detecting/processing unit,
   wherein the gantry and the patient pallet are relatively movable, and each of the plurality of integrated PET/CT detector modules include:
      a plurality of PET detectors,
      a flat-panel x-ray detector disposed in contact with a circumference side of the PET detectors in a line with the PET detectors and detecting a picture of the same position, and
      a read-out driver mounted at a rear end of the PET detectors and electrically connected with the flat-panel x-ray detector.

2. The integrated PET/CT system according to claim 1, wherein the x-ray tube produces fan beams and cone beams and rotates along the gantry.

3. The integrated PET/CT system according to claim 1, wherein each of the plurality of PET detectors include:
   a scintillator disposed in contact with the flat-panel x-ray detector;
   a light guide guiding light in contact with the scintillator;
   a control circuit disposed in contact with the read-out driver and having a pre-amplifier and a positioning circuit; and
   photomultipliers (PMTs) electrically connected in contact with the control circuit, which are covered by a magnetic shield preventing interference of a magnetic field, and are stacked in a plurality of layers.

4. The integrated PET/CT system according to claim 1, wherein each of the plurality of PET detectors include:
   a scintillator disposed in contact with the flat-panel x-ray detector; and
   a solid-state sensor disposed in contact with the scintillator.

5. The integrated PET/CT system according to claim 1, wherein for each of the integrated PET/CT detector modules a shape and an area of the flat-panel x-ray detector are the same as a shape and an area of the integrated PET/CT detector module.

* * * * *